US012679799B2

(12) United States Patent
Jovic et al.

(10) Patent No.: US 12,679,799 B2

(45) **Date of Patent: *Jul. 14, 2026**

(54) DIELECTRIC FLUID COMPOSITIONS COMPRISING LOW VISCOSITY MONOESTERS WITH IMPROVED LOW TEMPERATURE PERFORMANCE

(71) Applicant: Evonik Operations GmbH, Essen (DE)

(72) Inventors: Kristina Jovic, Singapore (SG); Roland Wilkens, Gernsheim (DE)

(73) Assignee: Evonik Operations GmbH, Essen (DE)

( * ) Notice: Subject to any disclaimer, the term of this patent is extended or adjusted under 35 U.S.C. 154(b) by 132 days.

This patent is subject to a terminal disclaimer.

(21) Appl. No.: 18/709,197

(22) PCT Filed: Nov. 10, 2022

(86) PCT No.: PCT/EP2022/081455

§ 371 (c)(1), (2) Date: May 10, 2024

(87) PCT Pub. No.: WO2023/088773

PCT Pub. Date: May 25, 2023

(65) Prior Publication Data

US 2025/0011275 A1 Jan. 9, 2025

(30) Foreign Application Priority Data

Nov. 17, 2021 (EP) .................................... 21208763

(51) Int. Cl.

*C07C 69/24* (2006.01)
*C09K 5/10* (2006.01)
*H01B 3/20* (2006.01)

(52) U.S. Cl.

CPC ................ *C07C 69/24* (2013.01); *C09K 5/10* (2013.01); *H01B 3/20* (2013.01)

(58) Field of Classification Search

CPC .............. C07C 69/24; C09K 5/10; H01B 3/20
See application file for complete search history.

(56) References Cited

U.S. PATENT DOCUMENTS

| | | | | |
|---|---|---|---|---|
| 5,949,017 | A | 9/1999 | Oommen et al. | |
| 8,466,248 | B2 * | 6/2013 | Meyer | C11D 3/3738 528/25 |
| 2013/0085090 | A1 | 4/2013 | Kim et al. | |
| 2024/0122831 | A1 * | 4/2024 | Friedrich | C12P 7/065 |

FOREIGN PATENT DOCUMENTS

| | | | |
|---|---|---|---|
| EP | 2 908 317 | A1 | 8/2015 |
| EP | 3 012 316 | A1 | 4/2016 |
| EP | 3 138 893 | A1 | 3/2017 |
| GB | 2525281 | A | 10/2015 |
| WO | 2013/159761 | A1 | 10/2013 |
| WO | 2015/174992 | A1 | 11/2015 |
| WO | 2022/175141 | A1 | 8/2022 |

OTHER PUBLICATIONS

Koshikari, "Development of Catalytic Ester Condensations and Hydrolysis of Esters toward Green Chemistry", Nagoya University Doctoral Thesis, 2012 (Year: 2012).*

Archived Nagoya University repository website, retrieved from the internet at <https://web.archive.org/web/20210618130207/https://nagoya.repo.nii.ac.jp/records/14552> on Nov. 14, 2025 (Year: 2021).*

Schulz, S., Yildizhan, S., Stritzke, K., Estrada, C., Gilbert, L.E., âMacrolides from the scent glands of the tropical butterflies Heliconius cydno and Heliconius pachinusâ, Org. Biomol. Chem., 2007, 5, 3434-3441 (Year: 2007).*

A. Paire, et al., "Siiver(II) Mediated Electrochemical Treatment of Selected Organics: Hydrocarbon Destruction Mechanism," Radiochimica Acta, vol. 78, 1997, pp. 137-143, XP055915924.

Areum Park, et al., "Structural and Experimental Evidence for the Enantiomeric Recognition toward a Bulky sec-Alcohol by Candida antarctica Lipase B," ACS Catalysis, vol. 6, No. 11, 2016, pp. 7458-7465, XP55915915.

Extended European Search Report for EP 21 20 8763 dated May 10, 2022.

International Search Report for PCT/EP2022/081455 dated Feb. 10, 2023.

Written Opinion for PCT/EP2022/081455 dated Feb. 10, 2023.

U.S. Appl. No. 18/546,509, filed Aug. 15, 2023 (Inventors: Achim Friedrich et al.; national stage of PCT/EP2022/053067 filed Feb. 9, 2022).

* cited by examiner

*Primary Examiner* — James C Goloboy

(74) *Attorney, Agent, or Firm* — Sughrue Mion, PLLC

(57) ABSTRACT

The invention relates to branched monoesters of formula (I), as well as to a dielectric fluid composition, intended for use as a cooling fluid for electrical equipment systems, comprising at least one of these branched monoesters of formula (I). The invention is also directed to a method of cooling electrical equipment systems by using the dielectric fluid compositions according to the invention.

16 Claims, No Drawings

DIELECTRIC FLUID COMPOSITIONS COMPRISING LOW VISCOSITY MONOESTERS WITH IMPROVED LOW TEMPERATURE PERFORMANCE

CROSS REFERENCE TO RELATED APPLICATIONS

This application is a National Stage of International Application No. PCT/EP2022/081455 filed Nov. 10, 2022, claiming priority based on European Patent Application No. 21208763.9 filed Nov. 17, 2021.

TECHNICAL FIELD OF THE INVENTION

The invention relates to branched monoesters of formula (I), as well as to a dielectric fluid composition, intended for use as a cooling fluid for electrical equipment systems, comprising at least one of these branched monoesters of formula (I). The invention is also directed to a method of cooling electrical equipment systems by using the dielectric fluid compositions according to the invention.

BACKGROUND OF THE INVENTION

In recent years, energy shortage and environmental concerns have had a tremendous impact on technological advancement. In the automotive industry, reduction of carbon footprint has become high priority and the demand for emission-free vehicles fueled by renewable energy sources, such as pure electric vehicles (EVs), hybrid electric vehicles (HEVs) and fuel cell electric vehicles, has gradually become more significant and is anticipated to increase drastically in the next 20 years. The energy for such vehicles is provided and stored in batteries having a high specific energy density. Various battery types are available for EVs and HEVs, such as lithium nickel manganese cobalt oxide, lithium iron phosphate, lithium cobalt oxide, lithium nickel cobalt aluminum oxide, lithium manganese oxide and sodium ion batteries.

To increase the performance of electric vehicles, large-scale batteries with a high current discharge are required. Due to the size and power output, these large-scale batteries generate a large amount of heat during rapid charge and discharge cycles at high current levels. Thus, batteries have to be thermally managed by cooling or dissipating heat to avoid battery malfunction and increase the lifetime of the battery.

Furthermore, the performance of the battery is temperature dependent. Depending on their type, batteries perform optimally only with a particular temperature range. Therefore, a proper thermal management allows optimizing battery performance.

Dielectric fluids mean fluids intended to be used for low to high voltage applications, e.g. computers, transformers, capacitors, high voltage cables, switchgear, and whose function is to provide electrical insulation, suppress corona and arcing, and to serve as a coolant in such electrical applications to carry and dissipate heat. Dielectric fluids include for example mineral oil-based fluids, natural ester-based fluid and synthetic ester-based fluids such as polyolesters.

Mineral oil-based dielectric fluids have been used extensively for a long time because they fulfill some of the above criteria. However, pure mineral oils do not dissipate so efficiently heat and there is still the need to investigate for better dielectric fluids with better thermal management properties.

Furthermore, the increase of environmental awareness has led to a growing interest in so-called green technologies, especially in the automobile industry. Consequently, ideal dielectric fluid should also be biodegradable, non-toxic and renewable. Mineral oil-based dielectric fluids are poorly biodegradable, relatively toxic and have no renewable source.

U.S. Pat. No. 5,949,017 discloses electrical transformers containing electrical insulation fluids comprising high oleic acid oil compositions as an alternative to mineral oil-based dielectric fluids. However, these dielectric fluids show a high viscosity in comparison to mineral oils, which is a disadvantage for heat dissipation.

WO2013159761A1 discloses compositions including esters of polyvalent alcohols that are esterified with fatty acids, partially unsaturated, from plant oils, and to the use thereof as cooling and insulating fluids for transformers. The esters used are polybranched esters which show a KV40 of approximately 30 $mm^2/s$ and a pour point of around minus 50° C.

WO2015/174992, US2013/085090 or EP3012316 disclose branched monoesters and lubricating oil compositions comprising the same. These documents do not deal with performance in cooling electrical equipment systems.

EP2908317 and EP3138893 disclose dielectric fluid compositions suitable for use in dielectric fluid compositions, wherein the ester composition comprises esters of an alcohol with a branched carboxylic acid. Both documents teach to use ester compositions comprising esters of branched carboxylic acids and polyols.

GB2525281A relates to ester dielectric fluid compositions suitable for use in electrical apparatus (e.g. transformers). The esters are derived from a reaction of (a) one or more alcohols selected from $C_2$ and $C_3$ polyols such as glycerol or ethylene glycol, and (b) one or more $C_4$ to $C_{14}$ carboxylic acids, wherein at least one of said acids is a branched acid (e.g. 2-ethyl-hexanoic acid). There are also one or more additives, such as antioxidants, metal deactivators or pour point depressants. The dielectric fluid compositions have a KV40 of around 16 $mm^2/s$ and a pour point of around minus 60° C.

Low viscosity of dielectric fluids is an extremely important parameter because it allows a more efficient heat dissipation through a more effective circulation, and therefore a better cooling of electric devices. Thus, the viscometric properties of dielectric fluids play an essential role in heat dissipation.

Therefore, the present invention aims at providing a new dielectric fluid composition with excellent performance in cooling electrical equipment systems, such as electric batteries, electric motors, electric transformers, electric capacitors, fluid-filled transmission lines, fluid-filled power cables, computers, data centers and power electronics. The new dielectric fluid compositions should not only have good electrical and thermal properties, but also have a low viscosity, be non-corrosive and have low flammability, while maintaining excellent low temperature performance.

BRIEF SUMMARY OF THE INVENTION

After thorough investigation, the inventors of the present invention have surprisingly found that a dielectric fluid composition comprising a branched monoester of Formula (I), as defined in the present invention, can be used as a heat transfer fluid for batteries and other electrical equipment to improve drastically the cooling performance of the electrical devices, in particular at low temperatures. The challenge was to combine improved heat dissipation performance, while still maintaining excellent low temperature properties of the dielectric fluid composition.

Indeed, developing one dielectric fluid composition with these properties shows great advantages because there is no need of additional pour point depressants.

According to a first aspect, the invention relates to branched monoesters of Formula (I) as defined in claim 1 and its dependent claims.

According to a second aspect, the invention relates to dielectric fluid compositions comprising the monoester of Formula (I) according to the present invention.

A third aspect of the invention is a method of cooling electrical equipment systems by using a dielectric fluid composition according to the present invention.

DETAILED DESCRIPTION OF THE INVENTION

Branched Monoesters According to the Invention

The present invention relates to branched monoesters A), wherein the branched monoester A) is of formula (I)

(I)

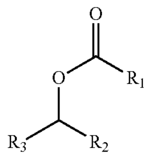

wherein $R_1$ is a linear alkyl residue with 3 to 13 carbon atoms, wherein each $R_2$ and $R_3$ is a linear alkyl residue with 5 carbon atoms.

Preferably, $R_1$ is a linear alkyl residue with 5 to 11 carbon atoms, more preferably with 5 to 7 carbon atoms.

According to the present invention, the alkyl residue $R_2$ and $R_5$ are both a linear alkyl residue with 5 carbon atoms.

According a preferred embodiment of the invention, the branched monoester A) is selected from 6-undecyllaurate, 6-undecylhexanoate, 6-undecyloctanoate or a mixture thereof.

In the present invention, the monoester A) may be prepared by the esterification reaction of an alcohol with an acid, as described for example in EP2155754B1.

Preferably, the alcohol can be prepared according to the process disclosed in the patent application WO2020/104429A1. This process has advantageously a low $CO_2$ footprint.

Dielectric Fluid Composition According to the Invention

The present invention also relates to a dielectric fluid composition comprising at least one branched monoester A), wherein the branched monoester A) is of formula (I)

(I)

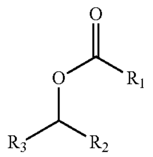

wherein $R_1$ is a linear alkyl residue with 3 to 13 carbon atoms, wherein each $R_2$ and $R_3$ is a linear alkyl residue with 5 carbon atoms.

In the context of the present invention, the term "at least" as used therein also means "one or more", or "one branched monoester A) or a mixture thereof".

All characteristics and preferences indicated above for the branched monoester A) of the present invention apply to the dielectric fluid compositions.

According to a preferred embodiment of the invention, the dielectric fluid composition comprises a branched monoester A) selected from 6-undecyllaurate, 6-undecylhexanoate, 6-undecyloctanoate, or a mixture thereof, more preferably selected from 6-undecylhexanoate, 6-undecyloctanoate, or a mixture thereof.

As shown in the experimental part below, the dielectric fluid compositions of the present invention have great electrical and heat transfer properties, have low flammability and are non-corrosive. They also have excellent low temperature performance. A further advantage of the dielectric fluid compositions according to the invention is their low viscosity, which allows a more efficient heat dissipation through a more effective circulation (in particular, thanks to a more efficient pumping), and therefore a better cooling of electric devices.

According to the present invention, it is preferred that the dielectric fluid composition has a kinematic viscosity at 40° C. from 2 $mm^2/s$ to 12 $mm^2/s$ according to ASTM D445 and a flash point of more than 110° C., more preferably of more than 140° C., according to ASTM D93.

According to the present invention, it is preferred that the dielectric fluid composition has a pour point below −70° C. (minus 70° C.) according to ASTM D5950, more preferably below −75° C. (minus 75° C.) according to ASTM D5950.

According to a preferred embodiment, the dielectric fluid composition of the invention has a Prandtl number below 90, at 40° C. and 1013 hPa (1 atm) pressure. More preferably, below 60, even more preferably below 55, at 40° C. and 1013 hPa (1 atm) pressure.

In the present invention, the Prandtl number (Pr) is calculated according to the formula below. The Prandtl number is a dimensionless quantity that puts the viscosity of a fluid in correlation with the thermal conductivity (see Bastian E. Rapp, in Microfluidics: Modelling, Mechanics and Mathematics, 2017). The Prandtl number is given as:

$$Pr=\vartheta/\alpha=\text{momentum diffusivity}/\text{thermal diffusivity}=(\mu/\rho/(k/(c_p\rho))=c_p\mu/k$$

wherein $\vartheta$: momentum diffusivity (kinematic viscosity) $\vartheta=\mu/\rho$; SI unit: $m^2/s$ $\alpha$: thermal diffusivity; SI unit: $m^2/s$ $\mu$: dynamic viscosity; SI unit: $Pa\cdot s=N\cdot s/m^2$ k: thermal conductivity; SI unit: $W/(m\cdot K)$ $c_p$: specific heat; SI unit: $J/(kg\cdot K)$ $\rho$: density; SI unit: $kg/m^3$ As shown in the experimental part below, the inventors of the present invention have surprisingly found out that the monoesters according to the invention and their corresponding inventive dielectric fluid compositions according to the invention have all small Prandtl numbers. This confirms that the dielectric fluid compositions according to the invention have high thermal conductivity and low viscosity, which is advantageous for thermal management in electric devices.

In particular, it has been advantageously observed that the inventive dielectric fluid compositions according to the invention all have high thermal conductivity values. This means that the dielectric fluids of the invention are capable of efficiently exchanging heat with an electrical device. Indeed, the higher the thermal conductivity, the better the heat transfer capacity.

According to a preferred embodiment of the invention, the dielectric fluid composition further comprises a base fluid component B) selected from the group consisting of polyol ester, saturated hydrocarbon, dicarboxylic acid ester, carbonate, ether, alcohol or a mixture thereof. Preferably, the component B) is glycerol trihexanoate, API group IV synthetic oil (preferably polyalphaolefin), API group III mineral oil or a mixture thereof. In the context of the present invention, component B) is a base fluid, different from the branched monoester A). Thus, preferably, the dielectric fluid composition comprises the branched monoester A) according to the invention as a first base fluid, and the above-indicated component B) as a second base fluid.

Preferably, the amounts of branched monoester A) and the base fluid B) add up to at least 90% by weight, more preferably add up to at least 95% by weight, based on the total weight of the dielectric fluid composition.

Preferably, the dielectric fluid composition may comprise an additive C) selected from the group consisting of defoamers, seal compatibility agents, antioxidants, yellow metal passivators, rust inhibitors, electrostatic discharge depressants, demulsifiers, dyes or a mixture thereof. The additive compounds C) correspond to typical additives used in thermal management fluids and are described in detail, inter alia, in T. Mang, W. Dresel (eds.): "Lubricants and Lubrication", Wiley-VCH, Weinheim 2001; R. M. Mortier, S. T. Orszulik (eds.): "Chemistry and Technology of Lubricants". Preferably, suitable yellow metal passivators are selected from the list consisting of imidazonines, imidazoles, thiazoles, thiadiazoles, triazoles, tolyltriazoles, pyradines, quinolines, morpholines or a mixture thereof.

Preferably, suitable rust inhibitors are selected from the list consisting of sulfonates, carboxylates, alkyl amines, amine carboxylates, amine borates, phosphates or a mixture thereof.

Preferably, suitable electrostatic discharge depressants are selected from the list consisting of ester quats, imidazolium quats, alkoxy alkyl quats, trialkyl monomethyl quats, monoalkyl trimethylquats, diamidoaminequats, benzyl quats, ethoxylated ether amines, ether diamines, fatty alcohols ethoxlates, ether amine oxides, ether amine quats or a mixture thereof.

Preferably, suitable demulsifiers are selected from the list consisting of polyalkoxylated phenols, polyalkoxylated polyols, polyalkoxylated polyamines or a mixture thereof.

Preferably, suitable defoamers are selected from the list consisting of silicone oils, fluorosilicone oils, fluoroalkyl ethers, polyacrylates or a mixture thereof.

Preferably, the seal compatibility agents are selected from the list consisting of adipate-ester, sebacate-ester, neopentylpolyol-ester, sulfolanes.

Preferably, the suitable antioxidants include phenol-based antioxidants and amine-based antioxidants.

In a preferred embodiment, the phenol-based antioxidants are selected from the list consisting of octadecyl-3-(3,5-di-tert-butyl-4-hydroxyphenyl) propionate; 4,4'-methylenebis (2,6-di-tert-butylphenol); 4,4'-bis(2,6-di-t-butylphenol); 4,4'-b is (2-methyl-6-t-butylphenol); 2,2'-methylenebis(4-ethyl-6-t-butylphenol); 2,2'-methylenebis(4-methyl-6-t-butyl phenol); 4,4'-butyl idenebis(3-methyl-6-t-butylphenol); 4,4'-isopropylidenebis(2,6-di-t-butylphenol); 2,2'-methylenebis(4-methyl-6-nonylphenol); 2,2'-isobutylidenebis(4,6-dimethylphenol); 2,2'-methylenebis(4-methyl-6-cyclohexylphenol); 2,6-di-t-butyl-4-methylphenol; 2,6-di-t-butyl-4-ethyl-phenol; 2,4-dimethyl-6-t-butylphenol; 2,6-di-t-amyl-p-cresol; 2,6-di-t-butyi-4-(N, N'-dimethylaminomethylphenol); 4,4'thiobis(2-methyl-6-t-butylphenol); 4,4'-thiobis(3-methyl-6-t-butylphenol); 2,2'-thiobis(4-methyl-6-t-butylphenol); bis(3-methyl-4-hydroxy-5-t-butylbenzyl) sulfide; bis(3,5-di-t-butyl-4-hydroxybenzyl) sulfide; n-octyl-3-(4-hydroxy-3,5-di-t-butylphenyl) propionate; n-octadecyl-3-(4-hydroxy-3,5-di-t-butylphenyl) propionate; 2,2'-thio [diethyl-bis-3-(3,5-di-t-butyl-4-hydroxyphenyl) propionate], or a mixture thereof. Even more preferred phenol-based antioxidants are bis-phenol-based antioxidants and ester group containing phenol-based antioxidants.

Amine-based antioxidants include, for example, monoalkyldiphenylamines such as monooctyldiphenylamine, monononyldiphenylamine; dialkyldiphenylamines such as 4,4'-dibutyldiphenylamine, 4,4'-dipentyldiphe nylamine, 4,4'-dihexyldiphenylamine, 4,4'-diheptyldiphenylamine, 4,4'-dioctyldiphenylamine, 4,4'-dinonyldiphenylamine; polyalkyldiphenylamines such as tetrabutyldiphenylamine, tetrahexyldiphenylamine, tetraoctyldiphenylamine, tetranonyldiphenylamine; naphthylamines, concretely alpha-naphthylamine, phenyl-alpha-naphthylamine and further alkyl-substituted phenyl-alpha-naphthylamines such as butylphenyl-alpha-naphthylamine, pentylphenyl-alpha-naphthylamine, hexylphenyl-alpha-naphthylamine, heptylphenyl-alpha-naphthylamine, octylphenyl-alpha-naphthylamine, nonylphenyl-alpha-naphthylamine. Of those, diphenylamines are preferred to naphthylamines, from the viewpoint of the antioxidation effect thereof.

Preferably, the dielectric fluid composition comprises 2 to 100% by weight of branched monoester A), 0 to 98% by weight of component B), and 0 to 5% by weight of additive C), based on the total weight of the dielectric fluid composition. More preferably, 5 to 100% by weight of branched monoester A), 0 to 95% by weight of component B), and 0 to 5% by weight of additive C), based on the total weight of the dielectric fluid composition.

According to a preferred embodiment, the amounts of A) to C) add up to at least 90% by weight, more preferably add up to at least 95% by weight, even more preferably add up to 100% by weight, based on the total weight of the dielectric fluid composition.

According to another preferred embodiment, the dielectric fluid composition of the invention consists of branched monoester A) of Formula (I), and all characteristics and preferences indicated above for the dielectric fluid composition apply to this preferred embodiment.

Preferably, the dielectric fluid compositions of the invention comprising at least one monoester A) of Formula (I) are biodegradable.

According to another preferred embodiment, the dielectric fluid compositions of the invention comprising at least one branched monoester A) of Formula (I) are halogen-free, which means that the dielectric fluid compositions do not comprise any halogen-containing components.

Preferably the dielectric fluid composition is produced with sustainable technology with a low carbon footprint and is halogen-free.

Method of Cooling Electrical Equipment Systems According to the Invention

According to another aspect of the present invention, the present invention also relates to a method of cooling electrical equipment systems by using a dielectric fluid composition as defined herein above.

Preferably, the electrical equipment system is selected from the group consisting of electric batteries, electric motors, electric transformers, electric capacitors, fluid-filled transmission lines, fluid-filled power cables, computers, data servers and power electronics.

Preferably, the method of cooling electrical equipment systems according to the invention is a direct liquid immersion cooling, in which heat is removed from the system by circulating liquid into direct contact with hot components.

EXPERIMENTAL PART

The invention is further illustrated in detail hereinafter with reference to examples and comparative examples, without any intention to limit the scope of the present invention.

| Abbreviations | |
| --- | --- |
| Cp @ 40° C. | specific heat capacity measured at 40° C. according ASTM D7896-14 |
| DPT | diisopentylterephthalate |
| Elect. Cond. | electrical conductivity was measured at 25° C. according to ASTM D2624 |
| FHE | C12/14 fattyalcoholhexanoate |
| FP | flash point according to ASTM D93 |
| GHE | glyceroltrihexanoate |
| KV40 | kinematic viscosity at 40° C. according to ASTM D445 |
| OptiCool-A Fluid | PAO ultra-low-viscosity dielectric heat transfer fluid comprising hydrogenated dimerization products of 1-decene and 1-dodenece, commercialized by the company DSI Venture |
| PAO 2 | polyalphaolefin with a KV40 of 5.10 mm$^2$/s |
| PN40 | Prandtl number @ 40° C. and 1013 hPa (1 atm) |
| PP | pour point according to ASTM D5950 |
| ULE | 6-undecyllaurate |
| UHE | 6-undecylhexanoate |
| UOE | 6-undecyloctanoate |
| Yubase 3 | hydrotreated light paraffinic base oil with a KV40 of 11.80 mm$^2$/s |
| Yubase 4 | hydrotreated heavy paraffinic base oil with a KV40 of 19.20 mm$^2$/s |
| λ @ 40° C. | thermal conductivity at 40° C. according to ASTM D7896-14 |

Test Methods

The kinematic viscosities of the dielectric fluid were measured at 40° C. according to ASTM D445 with no deviations.

Specific heat capacity and thermal conductivity was measured at 40° C. with the hot wire method according to ASTM D7896-14.

Pour point (PP) was measured according to ASTM D5950.

Flash point was measured with a closed-cup Pensky Martin set-up according to ASTM D93.

The electrical conductivity was measured at 25° C. according to ASTM D2624.

Monoesters of the Invention in Comparison with State-of-the-Art Components Suitable for Use as Dielectric Fluids

Inventive Examples

Synthesis of a Monoester A1 According to the Invention (ULE)

In a 4 Liter distillation flask equipped with a stir bar, water separator, reflux condenser, dropping funnel and internal thermometer, 482 g (2.8 mol) of 6-undecanol were mixed with 701 g (3.5 mol) of lauric acid and 1.75 g of a 50% aqueous solution of hypophosphorous acid (from Sigma Aldrich) (0.4% by mass of $H_3PO_2$ based on 6-undecanol)

heated to 240° C. with stirring. The course of the reaction was followed by GC analysis. The reaction had ended 6 hours after the start of boiling. Parts of this batch were removed, placed in a correspondingly smaller apparatus in which the water separator had been replaced by a distillation bridge. The excess lauric acid was distilled off at elevated temperature with stirring. The heating was then switched off and the batch was cooled to 80° C. By adding of water dropwise via the dropping funnel at a pressure of 27 to 33 hPa, resulted in further purification of the batch (principle of steam distillation). The mixture was stirred with 2% basic aluminum oxide and 2% active carbon for a further hour at a temperature of 100° C. The product was then separated off from the activated carbon and aluminum oxide by means of filtration.

Synthesis of a Monoester A2 According to the Invention (UHE)

For the synthesis of monoester A2 (UHE), 482 g (2.8 mol) of 6-undecanol were mixed with 407 g (3.5 mol) of hexanoic acid continuing with the same procedure as for the synthesis of monoester A1 as disclosed above.

Synthesis of a Monoester A3 According to the Invention (UOE)

For the synthesis of monoester A3 (UOE), 482 g (2.8 mol) of 6-undecanol were mixed with 505 g (3.5 mol) of octanoic acid continuing with the same procedure as for the synthesis of monoester A1 as disclosed above.

Comparative Examples

Comparative Example 1 (Comp. 1) Corresponds to FHE, a Linear C12-C14 Monoester 11.7 kg (100 mol) of hexanoic acid, 13.7 g (0.11% by weight, based on hexanoic acid) of tetrabutyl orthotitanate and 15.7 kg (80 mol) of Lorol were used as initial charge in a stirred flask with distillation bridge with reflux divider, stirrer, dropping funnel and thermometer, and were esterified at 200° C. Upon end of reaction the excess acid was removed by distillation at 180° C. and 3 mbar. The system was then cooled to 80° C. and neutralized using 10% strength by weight aqueous NaOH solution. Steam distillation was then carried out at a temperature of 80° C. and at a pressure from 20 to 5 mbar. The mixture was then dried at this temperature at 5 mbar. The mixture was stirred with active carbon at a temperature of 100° C. The product was then separated off from the activated carbon by means of filtration.

Comparative Example 2 (Comp. 2) Corresponds to Methyllaurate (Methyl Ester of Saturated Fatty Acid)

Comparative Example 3 (Comp. 3) Corresponds to Di-2-Ethylhexyl Sebacate, a Pure Synthetic Diester Base Stock Comparative Example 4 (Comp. 4) Corresponds to Di-(Isononyl) Adipate Comparative Example 5 (Comp. 5) Corresponds to Yubase 3 from SK Lubricants a Hydrotreated Light Paraffinic Base Oil All examples and their respective physical properties are shown in Table 1 below.

Results Discussion

The branched monoesters of the invention (Inventive Examples 1, 2 and 3) have very good thermal conductivity properties combined with low viscosity and excellent low temperature performance. In contrast, Comparative Examples 1 to 5 do not combine all together the above-indicated properties and thus do not perform so efficiently.

Comparative Examples 1 and 2 have similar low viscosities as Inventive Examples 2 and 3, but do not have a good low temperature performance (−6° C. and +3° C., respectively).

Comparative Examples 3, 4 and 5 show acceptable low temperature performance (with pour point values of −78° C. and −51° C., respectively). However, due to their high viscosity, their respective Prandtl numbers, which puts the viscosity of a fluid in correlation with its thermal conductivity as explained above, is high (PN40 of 136.5 and 128.7, respectively), thus much higher than the inventive monoesters according to the invention. Indeed, the branched monoesters A1, A2 and A3 according to the invention all have a Prandtl number below 85 (PN40 at 40° C. and 1013 hPa (1 atm)).

TABLE 2

Dielectric fluid formulations according to the invention and state-of-the-art dielectric fluid formulations (amounts below given in % by weight, based on the total weight of the formulation)

| | INVENTIVE EXAMPLES | | COMPARATIVE EXAMPLES | | |
|---|---|---|---|---|---|
| | F1 | F2 | Comp. F1 | Comp. F2 | Comp. F3 |
| Inv. monoester A2 | 10.0 | 85.7 | | | |
| GHE | | 3.0 | | | |
| PAO 2 | 90.0 | | | | 100 |
| Yubase 3 | | 6.6 | | | |
| Yubase 4 | | 3.0 | 34.4 | | |
| DPT | | 1.7 | | | |
| Comp. 1 | | | 65.6 | | |
| Opticool A | | | | 100 | |

The physical properties of the dielectric fluid formulations listed in Table 2 above are shown in Table 3 below.

From Table 3 below, it can be observed that the dielectric fluid compositions comprising the branched monoester according to the invention show great low temperature properties in combination with low Prandtl numbers at 40° C. and 1013 hPa (1 atm) and low viscosity. This confirms that the dielectric fluid compositions according to the invention have excellent performance in cooling electrical equipment systems.

Although the comparative dielectric fluid Comp. F1 has a higher flash point, it shows a poorer low temperature performance (only −9° C.), a higher viscosity (KV40 of 7.02 $mm^2/s$) and a higher Prandtl number (PN40 of 83.0).

The comparative dielectric fluid Comp. F2 shows a higher kinematic viscosity (KV40 of 6.50 $mm^2/s$), which does not provide a so efficient heat dissipation in comparison to dielectric fluids with a lower viscosity, because of an ineffective circulation and pumpability of the fluid in the electrical system.

Although the comparative dielectric fluid Comp. F3 has a comparable low temperature performance with a pour point of −75° C., it has a higher viscosity and a higher Prandtl number, thus not fulfilling all benefits of the inventive thermal dielectric fluid compositions comprising the branched monoesters of the present invention.

The thermal management results of the dielectric fluid compositions of the present invention confirm that dielectric

TABLE 1

Monoesters of the invention in comparison with state-of-the-art components suitable for use as dielectric fluids

| | | INVENTIVE EXAMPLES | | | COMPARATIVE EXAMPLES | | | | |
|---|---|---|---|---|---|---|---|---|---|
| | Units | Monoester A1 | Monoester A2 | Monoester A3 | Comp.1 | Comp.2 | Comp.3 | Comp.4 | Comp.5 |
| KV40 | $mm^2/s$ | 7.2 | 3.4 | 4.4 | 4.8 | 2.4 | 11.6 | 10.9 | 11.8 |
| Cp @ 40° C. | kJ/kg · K | 2.1 | 2.0 | 2.0 | 2.1 | 2.0 | 2.0 | 1.9 | 2.0 |
| λ @ 40° C. | mW/m · K | 148 | 137 | 140 | 150 | 146 | 151 | 147 | 135 |
| FP | ° C. | 190 | 146 | 158 | 171 | 128 | 218 | 217 | 191 |
| PP | ° C. | −27 | −99 | −96 | −6 | 3 | −78 | −51 | −33 |
| Elect. Cond. | nS/m | 0.04 | 0.02 | 0.06 | 0.01 | 2.50 | 0.10 | 0.20 | x |
| PN40 | | 85 | 43 | 52 | 56 | 28 | 137 | 129 | 142 |

x means "no electrical conductivity detected"

Dielectric Fluid Compositions

To prepare the dielectric fluid compositions, the components listed in Table 2 below were mixed at room temperature together.

fluid compositions comprising the branched monomers A) of Formula (I) do not only exhibit excellent low temperature properties, but also show very good electrical cooling performance as confirmed by the low Prandtil numbers. This combination of excellent low temperature properties, low viscosity and electrical cooling performance is not observed by the comparative dielectric fluids.

TABLE 3

Properties of the dielectric fluid formulations according to the invention in comparison with state-of-the-art dielectric fluid formulations

| | | INVENTIVE EXAMPLES | | COMPARATIVE EXAMPLES | | |
|---|---|---|---|---|---|---|
| | Units | F1 | F2 | Comp. F1 | Comp. F2 | Comp. F3 |
| KV40 | cSt | 4.88 | 4.14 | 7.02 | 6.50 | 5.10 |
| Cp @ 40° C. | kJ/kg · K | 2.11 | 1.95 | 2.12 | 2.08 | 2.11 |
| λ @ 40° C. | mW/m · K | 138.96 | 137.59 | 149.64 | 138.00 | 137.70 |
| FP | ° C. | 153 | 152 | 180 | 147 | 160 |
| PP | ° C. | −75 | −75 | −9 | −57 | −75 |
| Elect. Cond. | nS/m | 0.16 | 0.10 | 0.02 | x | x |
| PN40 | | 58.2 | 49.3 | 83.0 | 76.3 | 60.9 |

x means "no electrical conductivity detected"

The invention claimed is:

1. A branched monoester A), wherein the branched monoester A) is of formula (I)

(I)

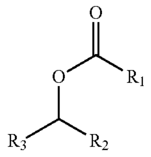

wherein $R_1$ is a linear alkyl residue with 3 to 13 carbon atoms, wherein each $R_2$ and $R_3$ is a linear alkyl residue with 5 carbon atoms, and the branched monoester A) does not include 6-undecyl laurate.

2. The branched monoester A) according to claim 1, wherein $R_1$ is a linear alkyl residue with 5 to 10 carbon atoms.

3. The branched monoester A) according to claim 1, wherein the branched monoester A) is selected from the group consisting of 6-undecylhexanoate, 6-undecyloctanoate and mixtures thereof.

4. A dielectric fluid composition, wherein the dielectric fluid composition comprises a branched monoester A) as defined in claim 1, or a mixture thereof.

5. The dielectric fluid composition according to claim 4, wherein the dielectric fluid composition further comprises a base fluid B) selected from the group consisting of polyol ester, saturated hydrocarbon, dicarboxylic acid ester, carbonate, ether, alcohol and mixtures thereof.

6. The dielectric fluid composition according to claim 4, wherein the dielectric fluid composition further comprises an additive C) selected from the group consisting of defoamers, seal compatibility agents, antioxidants, yellow metal passivators, rust inhibitors, electrostatic discharge depressants, demulsifiers, dyes and mixtures thereof.

7. The dielectric fluid composition according to claim 4, wherein the dielectric fluid composition comprises 2 to 100% by weight of branched monoester A), 0 to 98% by weight of base fluid B), and 0 to 5% by weight of additive C), based on the total weight of the dielectric fluid composition.

8. The dielectric fluid composition according to claim 7, wherein the amounts of A) to C) add up to at least 90% by weight, based on the total weight of the dielectric fluid composition.

9. A method of cooling an electrical equipment system comprising applying a dielectric fluid composition to the electrical equipment system, wherein the dielectric fluid composition comprises a branched monoester A) of formula (I), or a mixture thereof:

(I)

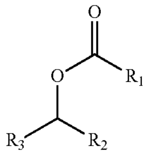

wherein $R_1$ is a linear alkyl residue with 3 to 13 carbon atoms, and wherein each $R_2$ and $R_3$ is a linear alkyl residue with 5 carbon atoms.

10. The method according to claim 9, wherein the dielectric fluid composition is applied to the electrical equipment system by direct liquid immersion.

11. The method according to claim 9, wherein $R_1$ is a linear alkyl residue with 5 to 11 carbon atoms.

12. The method according to claim 9, wherein the branched monoester A) is 6-undecyllaurate, 6-undecylhexanoate, 6-undecyloctanoate or a mixture thereof.

13. The method according to claim 9, wherein the dielectric fluid composition further comprises a base fluid B) selected from the group consisting of polyol ester, saturated hydrocarbon, dicarboxylic acid ester, carbonate, ether, alcohol and mixtures thereof.

14. The method according to claim 9, wherein the dielectric fluid composition further comprises an additive C) selected from the group consisting of defoamers, seal compatibility agents, antioxidants, yellow metal passivators, rust inhibitors, electrostatic discharge depressants, demulsifiers, dyes and mixtures thereof.

15. The method according to claim 9, wherein the dielectric fluid composition comprises 2 to 100% by weight of branched monoester A), 0 to 98% by weight of base fluid B), and 0 to 5% by weight of additive C), based on the total weight of the dielectric fluid composition.

16. The method according to claim 15, wherein the amounts of A) to C) add up to at least 90% by weight, based on the total weight of the dielectric fluid composition.

* * * * *